(12) United States Patent
Uchida et al.

(10) Patent No.: US 8,318,201 B2
(45) Date of Patent: Nov. 27, 2012

(54) METHOD OF STABILIZING DIARYLVINYLENE COMPOUND

(75) Inventors: Akihiro Uchida, Sunto-gun (JP); Yasuhiro Ishikawa, Sunto-gun (JP); Yasuhiko Ueno, Mishima (JP); Kiichiro Kaji, Machida (JP); Masaharu Aimoto, Sunto-gun (JP); Naoki Kaneko, Sunto-gun (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 1071 days.

(21) Appl. No.: 10/528,451

(22) PCT Filed: Sep. 29, 2004

(86) PCT No.: PCT/JP2004/014687
§ 371 (c)(1), (2), (4) Date: Mar. 18, 2005

(87) PCT Pub. No.: WO2005/030219
PCT Pub. Date: Apr. 7, 2005

(65) Prior Publication Data
US 2006/0134192 A1     Jun. 22, 2006

(30) Foreign Application Priority Data
Sep. 29, 2003  (JP) .................................. 2003-336944

(51) Int. Cl.
*A61K 31/522* (2006.01)
*A61K 9/20* (2006.01)

(52) U.S. Cl. .................................. 424/464; 514/263.31

(58) Field of Classification Search .................. 424/464; 514/263.31
See application file for complete search history.

(56) References Cited

U.S. PATENT DOCUMENTS

| | | | |
|---|---|---|---|
| 4,654,206 A * | 3/1987 | Okuda et al. ................. | 424/480 |
| 5,180,747 A | 1/1993 | Matsuda et al. ............... | 514/681 |
| 5,484,920 A | 1/1996 | Suzuki et al. ................. | 544/268 |
| 5,573,776 A * | 11/1996 | Harrison et al. ............... | 424/435 |
| 5,587,378 A | 12/1996 | Suzuki et al. ................. | 514/264 |
| 6,562,375 B1 * | 5/2003 | Sako et al. .................... | 424/486 |
| 2005/0176739 A1 * | 8/2005 | Hara et al. ................. | 514/263.24 |

FOREIGN PATENT DOCUMENTS

| | | |
|---|---|---|
| EP | 0 607 607 | 7/1994 |
| JP | 02-289513 | 11/1990 |
| JP | 09-164327 | 11/1991 |
| WO | WO 01/32182 | * 10/2001 |

OTHER PUBLICATIONS

Shimada, et al., "Adenosine A2A Antagonists with Potent Anti-Cataleptic Activity" Bioorg. Med. Chem. Lett., vol. 7 No. 18 (1997) 2349-52.
Béchard, et al., "Film coating: effect of titanium dioxide concentration and film thickness on the photostability of nifedipine", International Journal of Pharmaceutics, vol. 87, No. 1-3 (1992) 133-39.

* cited by examiner

*Primary Examiner* — Aradhana Sasan
(74) *Attorney, Agent, or Firm* — Fitzpatrick, Cella, Harper & Scinto

(57) ABSTRACT

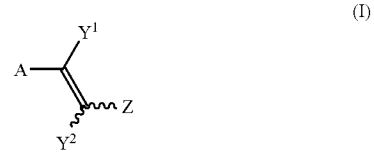

(I)

(wherein $Y^1$ and $Y^2$ may be the same or different and each represents a hydrogen atom, halogen or lower alkyl; and Z and A may be the same or different and each represents substituted or unsubstituted aryl, or substituted or unsubstituted heteroaryl)

The present invention provides, for example, a method for stabilization of a diarylvinylene compound such as a compound represented by the above formula (I) or the like, or a pharmaceutically acceptable salt thereof in a solid formulation containing the diarylvinylene compound or the pharmaceutically acceptable salt thereof, which comprises allowing an inorganic substance and/or a colorant to exist in the solid formulation, and the like.

6 Claims, No Drawings

METHOD OF STABILIZING DIARYLVINYLENE COMPOUND

TECHNICAL FIELD

The present invention relates to a method for stabilization of a diarylvinylene compound or a pharmaceutically acceptable salt thereof in a solid formulation containing the diarylvinylene compound or the pharmaceutically acceptable salt thereof.

BACKGROUND ART

It has been known that, due to its structural characteristics, in a diarylvinylene compound, that is a compound wherein two aromatic rings are bonded via vinylene, such as a compound represented by formula (I) described below [hereinafter, referred to as Compound (I)], for example, the vinylene moiety (a carbon-carbon double bond; conjugated olefin) is isomerized (isomerization from a Z-isomer to an E-isomer, or from an E-isomer to a Z-isomer), or two molecules thereof are intermolecularly bonded at the vinylene moiety to form a diner (dimerization). It has been further known that, for example, a xanthine derivative having a styryl structure in its structure represented by formula (IA) described below [hereinafter, referred to as Compound (IA)], more specifically, (E)-8-(3,4-dimethoxystyryl)-1,3-diethyl-7-methyl-3,7-dihydro-1H-purine-2,6-dione (hereinafter, referred to as Compound 1) is unstable particularly under irradiation of light and is easily isomerized at the vinylene moiety of the styryl structure, and that it is particularly unstable to light in a state of a solution [*Bioorg. Med. Chem. Lett.*, vol. 7, p. 2349-2352 (1997)]. On the other hand, it has been known that Compound (IA) or a pharmaceutically acceptable salt thereof shows adenosine $A_2$ receptor antagonistic activity and is therefore useful for the treatment of various diseases induced by hyperactivity of adenosine $A_2$ receptors such as Parkinson disease, senile dementia, depression or the like (e.g. EP0590919).

Additionally, for example, tablets containing lactose, potato starch, hydroxypropyl cellulose and Compound 1, and the like have been known (Japanese Published Unexamined Patent Application No. 211856/94).

As mentioned above, solid formulations containing Compound (I) or a pharmaceutically acceptable salt thereof, which have a general composition, have the problems of an increase in impurities caused by (a) isomerization, (b) dimerization or the like at the vinylene moiety due to the structural characteristics of the compound. Therefore, the greatest care is needed for its handling in the processes of preparing formulations, in preparing medicines in hospitals or pharmacies, in the storage of formulations, and the like. Solid formulations containing Compound (IA) or a pharmaceutically acceptable salt thereof, which have such general composition as described in Japanese Published Unexamined Patent Application No. 211856/94, have problems that (c) the hardness is insufficient, (d) the disintegration time is long, (e) the dissolution is likely to be delayed, and the like, in addition to the above problems.

DISCLOSURE OF THE INVENTION

The object of the present invention is to provide, for example, a method for stabilization of a diarylvinylene compound or a pharmaceutically acceptable salt thereof in a solid formulation containing the diarylvinylene compound or the pharmaceutically acceptable salt thereof (for example, a method of suppressing isomerization, dimerization or the like at the vinylene moiety of the diarylvinylene compound).

The present invention relates to the following (1) to (33).

(1) A method for stabilization of a diarylvinylene compound or a pharmaceutically acceptable salt thereof in a solid formulation containing the diarylvinylene compound or the pharmaceutically acceptable salt thereof, which comprises allowing an inorganic substance and/or a colorant to exist in the solid formulation.

(2) The method for stabilization according to the above (1), wherein the method for stabilization is a method of suppressing dimerization of the diarylvinylene compound or the pharmaceutically acceptable salt thereof.

(3) The method for stabilization according to the above (1) or (2), wherein the method for stabilization is a method of suppressing isomerization of the diarylvinylene compound or the pharmaceutically acceptable salt thereof.

(4) The method for stabilization according to any one of the above (1) to (3), wherein the diarylvinylene compound is a compound represented by formula (I)

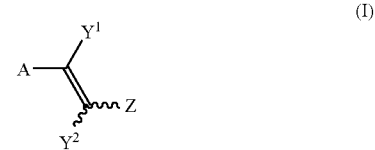

(wherein $Y^1$ and $Y^2$ may be the same or different and each represents a hydrogen atom, halogen or lower alkyl; and Z and A may be the same or different and, each represents substituted or unsubstituted aryl, or substituted or unsubstituted heteroaryl).

(5) The method for stabilization according to any one of the above (1) to (3), wherein the diarylvinylene compound is a xanthine derivative represented by formula (IA)

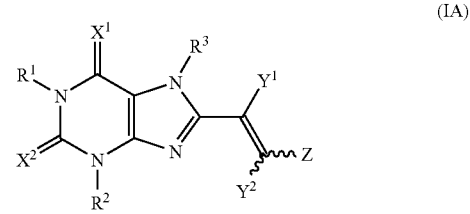

(wherein $Y^1$, $Y^2$ and Z have the same meanings as defined above, respectively; $R^1$, $R^2$ and $R^3$ may be the same or different and each represents a hydrogen atom, lower alkyl, lower alkenyl or lower alkynyl; and $X^1$ and $X^2$ may be the same or different and each represents an oxygen atom or a sulfur atom).

(6) The method for stabilization according to the above (5), wherein $Y^1$ and $Y^2$ each are a hydrogen atom; $X^1$ and $X^2$ each are an oxygen atom; $R^1$, $R^2$ and $R^3$ may be the same or different and each is a hydrogen atom or lower alkyl; and Z is formula (II)

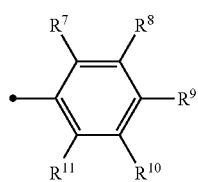

(wherein $R^7$, $R^8$, $R^9$, $R^{10}$ and $R^{11}$ may be the same or different and each represents a hydrogen atom, lower alkyl or lower alkoxy) or formula (III)

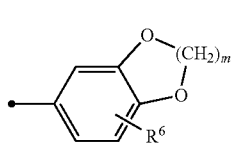

(wherein $R^6$ is a hydrogen atom, hydroxy, lower alkyl, lower alkoxy, halogen, nitro or amino; and m represents an integer of 1 to 3).

(7) The method for stabilization according to any one of the above (1) to (3), wherein the diarylvinylene compound is (E)-8-(3,4-dimethoxystyryl)-1,3-diethyl-7-methyl-3,7-dihydro-1H-purine-2,6-dione represented by formula (IB).

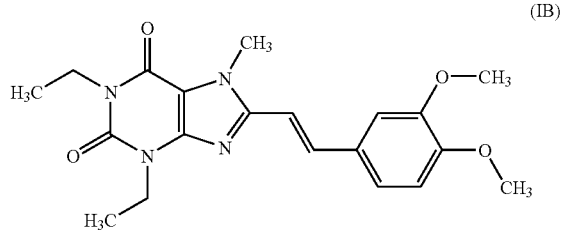

(8) The method for stabilization according to any one of the above (1) to (7), wherein a form of the solid formulation is a form in which a core containing the diarylvinylene compound or the pharmaceutically acceptable salt thereof is coated with a coated layer.

(9) The method for stabilization according to the above (8), wherein an inorganic substance and/or a colorant are/is allowed to exist in the coated layer.

(10) The method for stabilization according to any one of the above (1) to (9), wherein 0.001 to 10,000 part(s) by weight of the inorganic substance and/or 0.001 to 10,000 part(s) by weight of the colorant per 100 parts by weight of the diarylvinylene compound or the pharmaceutically acceptable salt thereof are/is allowed to exist.

(11) The method for stabilization according to the above (9), wherein 0.01 to 90 part(s) by weight of the inorganic substance and/or 0.01 to 70 part(s) by weight of the colorant per 100 parts by weight of the coated layer are/is allowed to exist, and wherein the total amount of the inorganic substance and the colorant is 0.01 to 90 part(s) by weight per 100 parts by weight of the coated layer.

(12) The method for stabilization according to any one of the above (1) to (11), wherein the inorganic substance is one or more inorganic substance(s) selected from the group consisting of titanium oxide, zinc oxide, magnesium oxide, talc, magnesium silicate, synthetic aluminum silicate, magnesium carbonate, calcium sulfate, aluminum sulfate and barium sulfate.

(13) The method for stabilization according to any one of the above (1) to (12), wherein the colorant is iron oxide.

(14) An agent for suppressing dimerization of a diarylvinylene compound or a pharmaceutically acceptable salt thereof, which comprises an inorganic substance and/or a colorant.

(15) The agent for suppressing dimerization according to the above (14), wherein the diarylvinylene compound is a compound represented by formula (I)

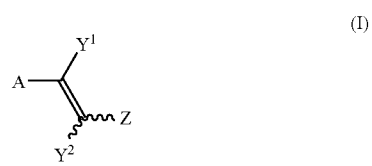

(wherein $Y^1$, $Y^2$, Z and A have the same meanings as defined above, respectively).

(16) The agent for suppressing dimerization according to the above (14), wherein the diarylvinylene compound is a xanthine derivative represented by formula (IA)

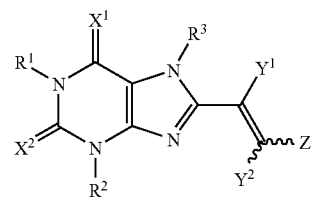

(wherein $Y^1$, $Y^2$, $X^1$, $X^2$, $R^1$, $R^2$, $R^3$ and Z have the same meanings as defined above, respectively).

(17) The agent for suppressing dimerization according to the above (16), wherein $Y^1$ and $Y^2$ each are a hydrogen atom, $X^1$ and $X^2$ each are an oxygen atom; $R^1$, $R^2$ and $R^3$ may be the same or different and each is a hydrogen atom or lower alkyl; and Z is formula (II)

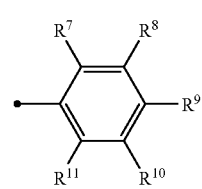

(wherein $R^7$, $R^8$, $R^9$, $R^{10}$ and $R^{11}$ have the same meanings as defined above, respectively) or formula (III)

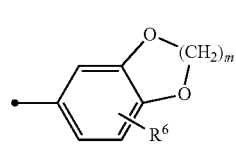

(wherein $R^6$ and m have the same meanings as defined above, respectively).

(18) The agent for suppressing dimerization according to the above (14), wherein the diarylvinylene compound is (E)-8-(3,4-dimethoxystyryl)-1,3-diethyl-7-methyl-3,7-dihydro-1H-purine-2,6-dione represented by formula (IB).

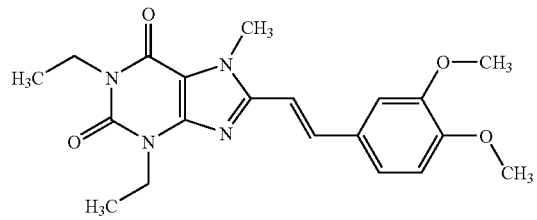

(IB)

(19) The agent for suppressing dimerization according to any one of the above (14) to (18), wherein the inorganic substance is one or more inorganic substance(s) selected from the group consisting of titanium oxide, zinc oxide, magnesium oxide, talc, magnesium silicate, synthetic aluminum silicate, magnesium carbonate, calcium sulfate, aluminum sulfate and barium sulfate.

(20) The agent for suppressing dimerization according to any one of the above (14) to (19), wherein the colorant is iron oxide.

(21) A solid formulation comprising a xanthine derivative represented by formula (IA)

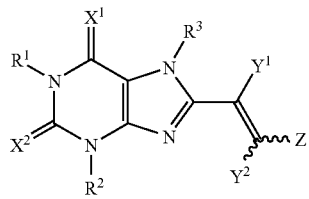

(IA)

(wherein $Y^1$, $Y^2$, $X^1$, $X^2$, $R^1$, $R^2$, $R^3$ and Z have the same meanings as defined above, respectively) or a pharmaceutically acceptable salt, and an inorganic substance and/or a colorant.

(22) The solid formulation according to the above (21), wherein $Y^1$ and $Y^2$ each are a hydrogen atom; $X^1$ and $X^2$ each are an oxygen atom; $R^1$, $R^2$ and $R^3$ may be the same or different and each is a hydrogen atom or lower alkyl; and Z is formula (II)

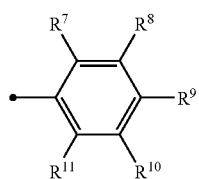

(II)

(wherein $R^7$, $R^8$, $R^9$, $R^{10}$ and $R^{11}$ have the same meanings as defined above, respectively) or formula (III)

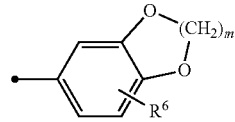

(III)

(wherein $R^6$ and m have the same meanings as defined above, respectively).

(23) The solid formulation according to the above (21), wherein the xanthine derivative is (E)-8-(3,4-dimethoxystyryl)-1,3-diethyl-7-methyl-3,7-dihydro-1H-purine-2,6-dione represented by formula (IB).

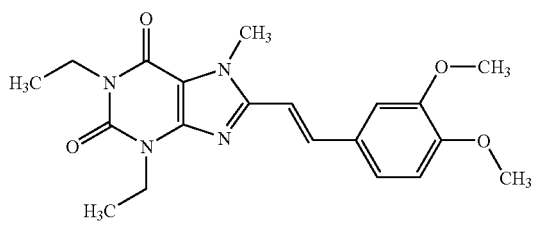

(IB)

(24) The solid formulation according to any one of the above (21) to (23), wherein a form of the solid formulation is a form in which a core containing the xanthine derivative or the pharmaceutically acceptable salt thereof is coated with a coated layer containing an inorganic substance and/or a colorant.

(25) The solid formulation according to any one of the above (21) to (24), wherein the inorganic substance is one or more inorganic substance(s) selected from the group consisting of titanium oxide, zinc oxide, magnesium oxide, talc, magnesium silicate, synthetic aluminum silicate, magnesium carbonate, calcium sulfate, aluminum sulfate and barium sulfate.

(26) The solid formulation according to any one of the above (21) to (25), wherein the colorant is iron oxide.

(27) Use of an inorganic substance and/or a colorant as an agent for suppressing dimerization of a diarylvinylene compound or a pharmaceutically acceptable salt thereof.

(28) The use, according to the above (27), wherein the diarylvinylene compound is a compound represented by formula (I)

(I)

(wherein $Y^1$, $Y^2$, Z and A have the same meanings as defined above, respectively).

(29) The use according to the above (27), wherein the diarylvinylene compound is a compound represented by formula (IA)

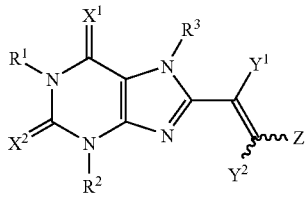

(wherein $Y^1$, $Y^2$, $X^1$, $X^2$, $R^1$, $R^2$, $R^3$ and Z have the same meanings as defined above, respectively).

(30) The use according to the above (29), wherein $Y^1$ and $Y^2$ each are a hydrogen atom; $X^1$ and $X^2$ each are an oxygen atom; $R^1$, $R^2$ and $R^3$ may be the same or different and each is a hydrogen atom or lower alkyl; and Z is formula (II)

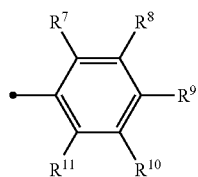

(wherein $R^7$, $R^8$, $R^9$, $R^{10}$ and $R^{11}$ have the same meanings as defined above, respectively) or formula (III)

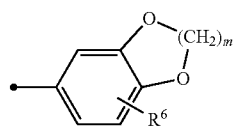

(wherein $R^6$ and m have the same meanings as defined above, respectively).

(31) The use according to the above (27), wherein the diarylvinylene compound is (E)-8-(3,4-dimethoxystyryl)-1,3-diethyl-7-methyl-3,7-dihydro-1H-purine-2,6-dione represented by formula (IB).

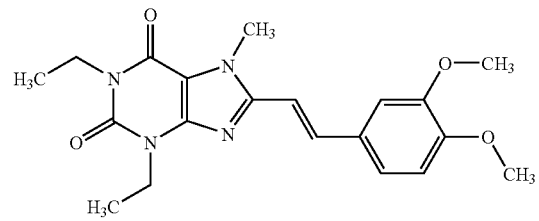

(32) The use according to any one of the above (27) to (31), wherein the inorganic substance is one or more inorganic substance(s) selected from the group consisting of titanium oxide, zinc oxide, magnesium oxide, talc, magnesium silicate, synthetic aluminum silicate, magnesium carbonate, calcium sulfate, aluminum sulfate and barium sulfate.

(33) The use according to any one of the above (27) to (32), wherein the colorant is iron oxide.

In the method for stabilization of the present invention:

(i) Examples of the method for stabilization of a diarylvinylene compound or a pharmaceutically acceptable salt thereof include a method of suppressing isomerization, dimerization or the like at the vinylene moiety of the diarylvinylene compound.

In the solid formulation comprising the diarylvinylene compound or the pharmaceutically acceptable salt thereof stabilized by the present invention:

(ii) The diarylvinylene compound is not particularly limited, so long as it is a compound wherein two aromatic rings are bonded via vinylene, and is a compound which has a possibility of isomerization at the vinylene moiety or that of formation of a dimer (dimerization) at the vinylene moiety as a result of intermolecular bonding of two molecules at the vinylene moiety. Examples thereof include RX-465, RX-549 and RX-512 [*British Journal of Cancer*, vol. 72, p. 1219-1223 (1995); *Anticancer Research*, vol. 17, p. 393-400 (1997)], CP-99711 [*Current Opinion in Therapeutic Patents, vol.* 9, p. 701-709 (1999)] and the like, and compounds mentioned in WO 03/043961, WO 03/042187, WO 03/037333, WO 03/000634, WO 02/24666, WO 02/00632, WO 01/70674, EP 00937722, WO 99/18068, EP 00846689, Japanese Published Unexamined Patent Application No. 268125/97, U.S. Pat. No. 5,656,655, WO 96/39391, Japanese Published Unexamined Patent Application No. 291127/96, GB 02297750, WO 96/04256, WO 96/04257, EP 00680953, WO 94/25462, WO 94/20455, EP 00607607, U.S. Pat. No. 5,198,452, WO 92/18481, EP 00503453, EP 00492249, EP 00466125, WO 90/16051, EP 00484587, U.S. Pat. No. 5,028,615, U.S. Pat. No. 4,920,130 or the like.

Specifically, for example, compounds represented by formula (I)

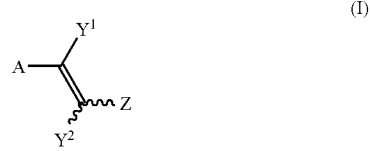

(wherein $Y^1$, $Y^2$, Z and A have the same meanings as defined above, respectively) are included. More Specifically, xanthine derivatives represented by formula (IA)

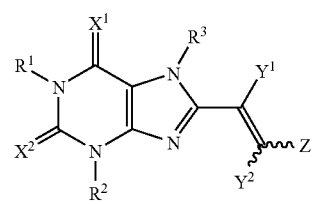

(wherein $Y^1$, $Y^2$, $X^1$, $X^2$, $R^1$, $R^2$, $R^3$ and Z have the same meanings as defined above, respectively) are included. Still more specifically, xanthine derivatives, that are Compound (IA) wherein $Y^1$ and $Y^2$ each are a hydrogen atom; $X^1$ and $X^2$ each are an oxygen atom; $R^1$, $R^2$ and $R^3$ may be the same or different and each represents a hydrogen atom or lower alkyl; and Z is formula (II)

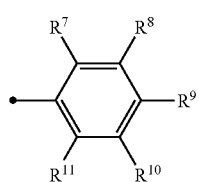

(II)

(wherein R⁷, R⁸, R⁹, R¹⁰ and R¹¹ have the same meanings as defined above, respectively) or formula (III)

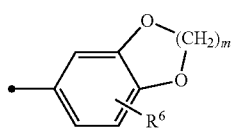

(III)

(wherein R⁶ and m have the same meanings as defined above, respectively), are included. Among them, (E)-8-(3,4-dimethoxystyryl)-1,3-diethyl-7-methyl-3,7-dihydro-1H-purine-2,6-dione is preferable.

In the definition for each group in formulae (I) and (IA):

The halogen means each atom of fluorine, chlorine, bromine and iodine.

Examples of the lower alkyl and the lower alkyl moiety in the lower alkoxy include straight-chain or branched alkyl groups having 1 to 6 carbon atoms and specifically include methyl, ethyl, propyl, isopropyl, butyl, isobutyl, sec-butyl, tert-butyl, pentyl, neopentyl, hexyl and the like.

Examples of the lower alkenyl include straight-chain or branched alkenyl groups having 2 to 6 carbon atoms and specifically include vinyl, allyl, methacryl, crotyl, 3-butenyl, 2-pentenyl, 4-pentenyl, 2-hexenyl, 5-hexenyl and the like.

Examples of the lower alkynyl include straight-chain or branched alkynyl groups having 2 to 6 carbon atoms and specifically include ethynyl, propargyl, 2-butynyl, 3-butynyl, 2-pentynyl, 4-pentynyl, 2-hexynyl, 5-hexynyl, 4-methyl-2-pentynyl and the like.

Examples of the aryl include aryl groups having 6 to 14 carbon atoms and specifically include phenyl, naphthyl, anthryl and the like.

Examples of the heteroaryl include 5-membered or 6-membered monocyclic heteroaryl containing at least one atom selected from a nitrogen atom, an oxygen atom and a sulfur atom and bicyclic or tricyclic condensed heteroaryl containing at least one atom selected from a nitrogen atom, an oxygen atom and a sulfur atom in which 3- to 8-membered rings are condensed and specifically include pyridyl, pyrazinyl, pyrimidinyl, pyridazinyl, benzimidazolyl, 2-oxobenzimidazolyl, benzotriazolyl, benzofuryl, benzothienyl, purinyl, benzoxazolyl, benzothiazolyl, 1,3-benzodioxolyl, 1,4-benzodioxanyl, 3,4-dihydro-2H-1,5-benzodioxepinyl, indazolyl, indolyl, isoindolyl, quinolyl, isoquinolyl, phthalazinyl, naphthyridinyl, quinoxalinyl, pyrrolyl, triazinyl, pyrazolyl, quinazolinyl, cinnolinyl, triazolyl, tetrazolyl, imidazolyl, oxazolyl, isoxazolyl, thiazolyl, isothiazolyl, thienyl, furyl, dihydroisoquinolyl, tetrahydroquinolyl, dihydrobenzopyranyl, 2,6-dioxo-3,7-dihydro-1H-purin-8-yl, 2,6-dithioxo-3,7-dihydro-1H-purin-8-yl and the like.

The substituted aryl and the substituted heteroaryl each have 1 to 3 substituents which may be the same or different, and examples of the substituents include lower alkyl, lower alkenyl, lower alkynyl, hydroxy, substituted or unsubstituted lower alkoxy, halogen, nitro, amino, lower alkylamino, di-lower alkylamino, trifluoromethyl, trifluoromethoxy, aralkyl, aralkyloxy, aryl, aryloxy, lower alkanoyl, lower alkanoyloxy, aroyl, aroyloxy, arylalkanoyloxy, carboxy, lower alkoxycarbonyl, lower alkylcarbamoyl, di-lower alkylcarbamoyl, sulfo, lower alkoxysulfonyl, lower alkylsulfamoyl, di-lower alkylsulfamoyl and the like.

In the above-mentioned examples of the substituents:

The lower alkyl moieties of the lower alkyl, the lower alkoxy, the lower alkylamino, the di-lower alkylamino, the lower alkanoyl, the lower alkanoyloxy, the lower alkoxycarbonyl, the lower alkylcarbamoyl, the di-lower alkylcarbamoyl, the lower alkoxysulfonyl, the lower alkylsulfamoyl and the di-lower alkylsulfamoyl have the same meaning as the lower alkyl described above; the halogen, the lower alkenyl and the lower alkynyl have the same meanings as described above, respectively; two lower alkyl moieties of the di-lower alkylamino, the di-lower alkylcarbamoyl and the di-lower alkylsulfamoyl each may be the same or different; the aryl moieties of the aryl and the aryloxy have the same meaning as the aryl described above; examples of the aralkyl moieties of the aralkyl and the aralkyloxy include benzyl, phenethyl and the like; examples of the aroyl moieties of the aroyl and the aroyloxy include benzoyl, naphthoyl and the like; and examples of the arylalkyl moiety of the arylalkanoyloxy include benzyl, phenethyl and the like. The substituted lower alkoxy has 1 to 3 substituents which may be the same or different, and examples of the substituents include hydroxy, lower alkoxy, halogen, amino, azido, carboxy, lower alkoxycarbonyl and the like; herein, the lower alkyl moieties of the lower alkoxy and the lower alkoxycarbonyl have the same meaning as the lower alkyl described above; and the halogen has the same meaning as described above.

Examples of the pharmaceutically acceptable salts of the diarylvinylene compound include pharmaceutically acceptable acid addition salts, metal salts, ammonium salts, organic amine addition salts, amino acid addition salts and the like.

Examples of the pharmaceutically acceptable acid addition salts of the diarylvinylene compound include inorganic acid salts such as a hydrochloride, a sulfate and a phosphate, and organic acid salts such as an acetate, a maleate, a fumarate, a tartrate, a citrate and a methanesulfonate; examples of the pharmaceutically acceptable metal salt include alkali metal salts such as a sodium salt and a potassium salt, alkaline earth metal salts such as a magnesium salt and a calcium salt, an aluminium salt, a zinc salt, and the like; the pharmaceutically acceptable ammonium salts include ammonium, tetramethylammonium and the like; examples of the pharmaceutically acceptable organic amine addition salt include addition salts with morpholine, piperidine or the like; and examples of the pharmaceutically acceptable amino acid addition salt include addition salts with lysine, glycine, phenylalanine or the like.

The diarylvinylene compound or a pharmaceutically acceptable salt thereof used for the solid formulation, which contains the diarylvinylene compound or a pharmaceutically acceptable salt stabilized by the present invention, is not particularly limited, so long as it is a solid such as a powder, crystals or a mass. For example, Compound (I) can be obtained by known methods [e.g., *British Journal of Cancer*, vol. 72, p. 1219-1223 (1995); *Anticancer Research*, vol. 17, p. 393-400 (1997); *Current Opinion in Therapeutic Patents*, vol. 9, p. 701-709 (1999); WO 03/043961; WO 03/042187; WO 03/037333; WO 03/000634; WO 02/24666; WO 02/00632; WO 01/70674; EP 00937722; WO 99/18068; EP 00846689; Japanese Published Unexamined Patent Application No. 268125/97; U.S. Pat. No. 5,656,655; WO 96/39391; Japanese Published Unexamined Patent Application No. 291127/96;

GB 02297750; WO 96/04256; WO 96/04257; EP 00680953; WO 94/25462; WO 94/20455; EP 00607607; U.S. Pat. No. 5,198,452; WO 92/18481; EP 00503453; EP 00492249; EP 00466125; WO 90/16051; EP 00484587; U.S. Pat. No. 5,028, 615 and U.S. Pat. No. 4,920,130] or modified methods thereof.

More specifically, in the case of Compound (IA), examples include the crystalline Compound (IA) having a crystallinity of 20% or more, or a pharmaceutically acceptable salt thereof. Among them, the crystalline Compound (IA) having a crystallinity of 30% or more, or a pharmaceutically acceptable salt thereof is preferable, and the crystalline Compound (IA) a crystallinity of 40% or more or a pharmaceutically acceptable salt thereof is more preferable. The crystallinity of Compound (IA) or a pharmaceutically acceptable salt thereof means the relative amount of "the crystalline Compound (IA) or a pharmaceutically acceptable salt thereof" in "Compound (IA) or a pharmaceutically acceptable salt thereof", and can be calculated from the following formula.

$$\text{The Crystallinity (\%)} = \frac{\text{Amount of "the crystalline Compound (IA) or a pharmaceutically acceptable salt thereof"}}{\text{Amount of "Compound (IA) or a pharmaceutically acceptable salt thereof"}} \times 100$$

The amount of "Compound (IA) or a pharmaceutically acceptable salt thereof" means the total amount of "the crystalline Compound (IA) or a pharmaceutically acceptable salt thereof" and "an amorphous Compound (IA) or a pharmaceutically acceptable salt thereof". The crystallinity can be calculated by measuring the integral intensity of the diffraction peak at a specific angle of diffraction 2θ, for example by a powder X-ray diffractmeter (e.g., JDX8030; manufactured by JEOL Ltd.), that is the crystallinity can be determined as the ratio of the integral intensity of the diffraction peak of a sample measured to the integral intensity of the diffraction peak of a standard sample. The proportion of "the crystalline Compound (IA) or a pharmaceutically acceptable salt thereof" in the standard sample is 100% (the crystallinity of 100%). These can be obtained by methods described in Japanese Published Unexamined Patent Application No. 211856/ 94, EP 0 590 919, Japanese Published Unexamined Patent Application No. 040652/97 or the like, or modified methods thereof.

In addition, among the crystalline Compound (IA) having the crystallinity of 20% or more, or a pharmaceutically acceptable salt thereof, such compound that having an average particle size of 50 μm or less, or a pharmaceutically acceptable salt thereof is preferable. Particularly, the crystalline Compound (IA) having an average particle size of 0.5 to 20 μm and the crystallinity of 20% or more, or a pharmaceutically acceptable salt thereof is more preferable. In this connection, the average particle size can be measured, by using, for example, a laser diffraction/scattering particle size distribution analyzer (e.g., MASTERSIZER 2000 Ver. 2.00 J; manufactured by MALVERN instruments) or an image analyzer (e.g., LUZEX® AP; manufactured by NIRECO Co.), etc., and can be calculated from the mean of the particle size distribution. These can be prepared by pulverization and/or sieving the crystalline Compound (IA) having the crystallinity of 20% or more or a pharmaceutically acceptable salt thereof, which is obtained by methods described in Japanese Published Unexamined Patent Application No. 211856/94, EP 0 590 919, Japanese Published Unexamined Patent Application No. 040652/97 or the like, or modified method thereof. The pulverization and the sieving may be appropriately carried out in combination several times. The pulverization can be carried out by a pulverizer generally used, such as a mortar, Mechanomill® (manufactured by Okada Seiko Co., Ltd.), and a jet mill. In the pulverization, the pulverization conditions, such as the rotational speed of the pulverizer; the feed rate of the crystalline Compound (IA) having a crystallinity of 20% or more, or a pharmaceutically acceptable salt thereof; the time required for pulverization; and the like, are appropriately controlled to obtain the crystalline Compound (IA) having a desired average particle size and/or a desired crystallinity, or a pharmaceutically acceptable salt thereof. Among them, the pulverization by the jet mill is preferable, and the crystalline Compound (IA) having a crystallinity of 20% or more, or a pharmaceutically acceptable salt thereof can be pulverized, by feeding the crystalline Compound (IA) having a crystallinity of 20% or more, or a pharmaceutically acceptable salt thereof, at a rate of 10 to 1,000 g/min and under pressure of 0.01 to 1.0 MPa.

The amount of the diarylvinylene compound or a pharmaceutically acceptable salt thereof, which is stabilized by the present invention, in the solid formulation is not particularly limited. In case of Compound 1, for example, the proportion of Compound 1 in the solid formulation is preferably 1 to 50%, more preferably 2 to 30%, still more preferably 5 to 20% of the total weight of the solid formulation.

(iii) A dosage form of the solid formulation containing the diarylvinylene compound or the pharmaceutically acceptable salt thereof, which is stabilized by the present invention, is not particularly limited. Examples thereof include tablets, capsules, granules and the like. Among them, tablets are preferable. Specifically, among said solid formulation, a solid formulation having a form in which a core containing the diarylvinylene compound or the pharmaceutically acceptable salt thereof is coated with a coated layer is preferable. Among them, a solid formulation in which an inorganic substance and/or a colorant exist(s) in the coated layer is more preferable.

In addition, the solid formulation may contain additives, which are generally used in solid formulations, such as a vehicle, a binder, a disintegrator and the like. In the solid formulation having the form in which the core is coated with a coated layer, a solid formulation in which the core contains a vehicle, a binder, a disintegrator and the like is preferable.

(iii-a). The vehicle is not particularly limited, so long as it is generally used in solid formulations. Examples of the vehicle include a sugar, starch, calcium citrate, calcium monohydrogen phosphate, microcrystalline cellulose, corn starch and magnesium aluminometasilicate and the like, which may be used alone or by combining these two or more. Among them, it is preferable that microcrystalline cellulose is used alone or microcrystalline cellulose is used in combination with one or more other vehicle(s). Examples of one or more of other vehicle (s) include the examples of the vehicle described above, excluding microcrystalline cellulose.

When microcrystalline cellulose is used in combination with one or more of other vehicle(s), a combination of microcrystalline cellulose and starch or a sugar is preferable, and specifically, a combination of microcrystalline cellulose and a sugar is more preferable.

Examples of the sugar include lactose, sucrose, glucose, cyclodextrin, D-mannitol, xylitol, erythritol, sorbitol, maltitol and the like. Among them, lactose, sucrose, glucose, cyclodextrin or D-mannitol is preferable, and lactose is more preferable.

The microcrystalline cellulose is not particularly limited, so long as it is generally used in solid formulations. Examples of the microcrystalline cellulose include microcrystalline cellulose or powdered cellulose, which is commercially available.

The vehicle content of the solid formulation is not particularly limited, but is preferably 0.5 to 99.5%, more preferably 1 to 95%, still more preferably 10 to 90%, most preferably 20 to 85% of the total weight of the solid formulation.

When microcrystalline cellulose is used in combination with one or more of other vehicle(s), as to a combination ratio of those is preferably 1 to 9 parts by weight, more preferably 1 to 5 parts by weight, still more preferably 1.5 to 3 parts by weight of one or more of other vehicle(s), such as starch or a sugar, per 1.0 part by weight of microcrystalline cellulose; and the microcrystalline cellulose content of is not particularly limited, but is preferably 1 to 75%, more preferably 5 to 50% or, still more preferably, 10 to 30% in the total weight of the solid formulation.

(iii-b) The binder is not particularly limited, so long as it is generally used in solid formulations. Examples of the binder include hydroxypropylcellulose (HPC), hydroxypropylmethylcellulose (HPMC), polyvinylpyrrolidone (PVP), polyvinyl alcohol, α-starch and the like. Among them, HPC, HPMC, PVP or polyvinyl alcohol is preferable, and specifically, polyvinyl alcohol is more preferable. In addition, as the polyvinyl alcohol, polyvinyl alcohol with a polymerization degree of 250 to 5,000 is preferable. Particularly, polyvinyl alcohol with a polymerization degree of 500 to 5,000 is more preferable.

The binder content of the solid formulation is not particularly limited, but is preferably 0.1 to 10%, more preferably 0.5 to 7%, still more preferably 1 to 5% of the total weight of the solid formulation.

(iii-c) The disintegrator is not particularly limited, so long as it is generally used in solid formulations. Examples of the disintegrator include sodium alginate, croscarmellose sodium, sodium starch glycolate, lower substituted hydroxypropylcellulose, crospovidone, croscarmellose calcium and the like. Among them, lower substituted hydroxypropylcellulose, crospovidone, croscarmellose sodium or sodium starch is preferable, and specifically, glycolate crospovidone is more preferable.

The disintegrator content of the solid formulation is not particularly limited, but is preferably 0.5 to 20%, more preferably 1 to 15%, still more preferably 3 to 10% of the total weight of the solid formulation.

(iii-d) In addition, the solid formulation and the core and the coated layer in the solid formulation having the form in which the core is coated with the coated layer each may contain other additives, which are generally used in solid formulations, such as a lubricant, a surfactant and a plasticizer.

Examples of the lubricant include magnesium stearate, calcium stearate, talc, light anhydrous silicic acid, hydrated silicon dioxide and the like. Examples of the surfactant include phospholipid, glycerol fatty acid esters (e.g., triacetin and the like), sorbitan fatty acid esters, polyoxyethylene fatty acid esters, polyethylene glycol fatty acid esters, polyoxyethylene hydrogenated castor oil, polyoxyethylene alkyl ether, sucrose fatty acid esters and the like. Examples of the plasticizer include triacetin, vegetable oils, polyethyleneglycol and the like.

Examples of a coating form include sugar coating and film coating. Among them, film coating is preferable.

The coat layer used for the coating comprises a coating composition containing a coating agent. The weight of the coated layer is not particularly limited, but is preferably 0.1 to 100 part(s) by weight, more preferably 0.5 to 50 part(s) by weight or, still more preferably 1 to 30 part (s) by weight per 100 parts by weight of the core.

Examples of the coating agent are calcium carbonate, lactose, sucrose, calcium monohydrogenephosphate, talc, acacia, HPC, HPMC, ethylcellulose, polyethylene glycol, polyoxyethylene [105] polyoxypropylene [5] glycol, polyoxyethylene [160] polyoxypropylene [30] glycol, glycol, methacrylic acid copolymer, polyvinyl alcohol, PVP, enteric polymer (e.g., hydroxypropylmethylcellulose phthalate, cellulose acetate phthalate and carboxymethylethylcellulose) and the like.

Amount of the coating agent is preferably 0.1 to 99 part(s) by weight, more preferably 1 to 90 parts by weight and, still more preferably, 5 to 85 parts by weight per 100 parts by weight of the coat.

(iv) The inorganic substance is not particularly limited, so long as it is generally used in solid formulations. Examples of the inorganic substance include titanium oxide, zinc oxide, magnesium oxide, talc, magnesium silicate, synthetic aluminum silicate, magnesium carbonate, calcium sulfate, aluminum sulfate, barium sulfate and the like, which may be used alone or by combining these two or more. Among them, titanium oxide, zinc oxide, talc, barium sulfate or a mixture thereof is preferable, and specifically, titanium oxide, talc or barium sulfate is more preferable. And also, the inorganic substance can be appropriately used in combination with the colorant described below, but when the inorganic substance is used alone, titanium oxide, talc or a mixture of talc and barium sulfate is more preferable.

These inorganic substances may be in any crystal forms and its particle size is not particularly limited. Specifically, examples of titanium oxide are that in a crystal form such as a rutile type and an anatase type.

The amount of the inorganic substance used in the method for stabilization of the present invention (i.e., the inorganic substance content of the solid formulation) is not particularly limited, but is preferably 0.001 part by weight to 10,000 parts by weight, more preferably 0.01 to 1,000 part(s) by weight or, still more preferably, 0.1 to 500 part(s) by weight per 100 parts by weight of the diarylvinylene compound or the pharmaceutically acceptable salt thereof.

In the solid formulation having the form in which the core containing the diarylvinylene compound or the pharmaceutically acceptable salt, which is stabilized by the present invention, is coated with a coated layer, when the inorganic substance exists in the coated layer, its amount is not particularly limited, but is preferably 0.01 to 90 part(s) by weight, more preferably 0.05 to 70 part (s) by weight or, still more preferably, 0.1 to 50 part(s) by weight per 100 parts by weight of the coated layer.

(v) The colorant is not particularly limited, but for example, a colorant assuming a yellow, red or black color is preferable, and these may be used alone or by combining two or more. Specifically, examples of the colorant assuming a yellow color include yellow ferric oxide, yellow oxide of iron, food yellow No. 4 aluminum lake, red oxide of iron and the like; examples of the colorant assuming a red color include red ferric oxide, food red No. 2, food red No. 3, food red No. 102 and the like; and examples of the colorant assuming a black color include black oxide of iron, carbon black, medicinal carbon and the like. Among the colorants mentioned above, iron oxide such as yellow ferric oxide, yellow oxide of iron, red ferric oxide and black oxide of iron is more preferable. Among them, one or more iron oxide(s) selected from the group consisting of yellow ferric oxide, red ferric oxide and black oxide of iron are/is preferable, and yellow ferric oxide, red ferric oxide or a combination of yellow ferric oxide and red ferric oxide is still more preferable.

The amount of the colorant used in the method for stabilization of the present invention (i.e., the colorant content of the solid formulation) is not particularly limited, but is preferably 0.001 part by weight to 10,000 parts by weight, more preferably 0.01 to 1,000 part(s) by weight or, still more preferably, 0.1 to 500 part (s) by weight per 100 parts by weight of the diarylvinylene compound or the pharmaceutically acceptable salt thereof.

In the solid formulation having the form in which the core containing the diarylvinylene compound or the pharmaceutically acceptable salt, which is stabilized by the present invention, is coated with a coated layer, when the colorant exists in the coated layer, its amount is not particularly limited, but is preferably 0.01 to 70 part(s) by weight, more preferably 0.05 to 50 part(s) by weight or, still more preferably, 0.1 to 30 part(s) by weight per 100 parts by weight of the coated layer.

In the method for stabilization of the present invention, when both inorganic substance and colorant exist in the solid formulation, a combination of those is not particularly limited. Examples of the combination include titanium oxide and iron oxide; talc and iron oxide; and the like. Among them, a combination of titanium oxide and yellow ferric oxide; titanium oxide and red ferric oxide; titanium oxide and black oxide of iron; talc and yellow ferric oxide; talc and red ferric oxide; or talc and black oxide of iron is preferable.

A combination ratio of those not particularly limited, but is preferably 1 to 50 part(s) by weight, more preferably 1 to 30 part(s) by weight, still more preferably 5 to 20 parts by weight of the colorant, per 1.0 part by weight of the inorganic substance.

Among the solid formulation having the form in which the core containing the diarylvinylene compound or the pharmaceutically acceptable salt, which is stabilized by the present invention, is coated with a coated layer, a solid formulation in which both inorganic substance and colorant exists in the coated layer is preferable.

When both inorganic substance and colorant exists in the coated layer, the total amount of the inorganic substance and the colorant is not particularly limited, but is preferably 0.01 to 90 part(s) by weight, more preferably 0.05 to 70 part(s) by weight or, still more preferably, 0.1 to 50 part(s) by weight per 100 parts by weight of the coated layer.

(vi) The agent for suppressing dimerization of the present invention can contain other additives which are not particularly limited, and any composition depending upon its use is acceptable, so long as it can suppress dimerization of the diarylvinylene compound or contains an inorganic substance and/or a colorant and the pharmaceutically acceptable salt thereof. For example, it can be used for stabilization of the diarylvinylene compound or the pharmaceutically acceptable salt thereof in the solid formulation containing the diarylvinylene compound or the pharmaceutically acceptable salt thereof.

Examples of the inorganic substance and the colorant include the same as those mentioned above in the method for stabilization, respectively.

When they are used for suppressing dimerization of the diarylvinylene compound or the pharmaceutically acceptable salt thereof in a solid formulation containing the diarylvinylene compound or the pharmaceutically acceptable salt thereof, amounts of and a combination ratio of the inorganic substance and/or the colorant in the solid formulation are the same as those mentioned above in the method for stabilization.

The agent for suppressing dimerization can be used, for example, as an ingredient of a coated layer for coating the core containing the diarylvinylene compound or the pharmaceutically acceptable salt thereof. Among them, an agent for suppressing dimerization which contains both inorganic substance and colorant is preferably used.

When the agent for suppressing dimerization is used as the ingredient of a coated layer, the agent for suppressing dimerization may contain additives, which are generally used in solid formulations, such as a lubricant, a surfactant and a plasticizer. Examples of the lubricant, the surfactant agent and the plasticizer include the same as those mentioned above in the method for stabilization, respectively.

The method for stabilization (such as a method of suppressing dimerization, a method of suppressing isomerization and the like) of the present invention can be carried out, for example, by the following method for the production of a solid formulation. Namely, it can be carried out by making diarylvinylene compound or a pharmaceutically acceptable salt thereof into formulations in which the inorganic substance and/or the chlorant exist(s).

The solid formulation containing a diarylvinylene compound or a pharmaceutically acceptable salt thereof stabilized by the present invention is prepared by general methods which are carried out in manufacturing pharmacy. A manufacturing method of the solid formulation is not particularly limited, but is carried out by the processes of preparing formulations generally used in the technical field of pharmaceutics, if necessary, such as a mixing process, a pulverizing process, a sieving process, a granulation process, a milling process, a tableting process, a drying process, a capsule-filling process, a coating process and the like, appropriately in combination. For example, the solid formulation can be prepared according to the following manufacturing method.

[Manufacturing Method of Tablets]

The tablets of the present invention can be prepared by a method generally used in the technical field of pharmaceutics, such as compression molding or the like. Examples of the method include a method which consists of mixing the each component as described above in a blender or the like, and then tableting the resulting mixture as it is, by a tablet-pressing machine, to make the tablets; a method which consists of granulating the each component as described above, and then tableting the resulting granules to form the tablets; and the like. The pressure for tableting can appropriately be selected, for example, within a range of 300 to 3,000 kg/cm$^2$. The size of the tablet is not particularly limited, but the total weight of the tablet is preferably 20 to 3,000 mg per tablet and the particle size of the tablet is preferably 5 to 15 mm.

The granule can be prepared, for example, by a wet granulation, a dry granulation or the like. Examples of the wet granulation include extrusion granulation (using a column-shaped granule manufacturing apparatus), wet high-share granulation, fluidized bed granulation or the like. More specifically, the examples include a method, which consists of processes comprising:

(1a) mixing the diarylvinylene compound or the pharmaceutically acceptable salt thereof, and the additives such as the disintegrator and the like, and (2a) spraying a solution of the inorganic substance and/or the colorant, and binder onto the resulting mixture to prepare a granule; or (1b) mixing the diarylvinylene compound or the pharmaceutically acceptable salt thereof, the additives such as the disintegrator and the like, and the inorganic substance and/or the colorant, and (2b) spraying a solution of binder onto the resulting mixture to prepare a granule; and then (3) drying the resulting granule; and the like.

Examples of the solvent used in the spraying are water, ethanol, isopropyl alcohol and a mixture thereof. Among them, water is preferable. Examples of the dry granulation include a method, which consist of processes comprising (1) forming a flake by a commercially available roller compactor or forming a pellet by a tableting machine, and then (2) comminuting the resulting flake or pellet by a commercially available a cutting mill or a screen mill to obtain a granule; and the like.

In addition, according to a general method, a core (a core tablet) is preparing by using each ingredient as described above excluding the inorganic substance and the colorant in a manner similar to that in the above methods, and then the resulting core tablet is coated with a suspension, in which the coating composition containing the inorganic substance and/or the colorant is dispersed, to form the coated layer thereon and obtain the tablet. Examples of the solvent in which the coating composition is dispersed include water, ethanol, isopropanol and a mixed solvent thereof. Among them, water is preferable.

The coating may be carried out by using, for example, a conventionally used type such as coating machine of a pan type, coating machine of an aeration type, fluidized bed coating apparatus and coating apparatus of a tumbling flow type.

[Manufacturing Method of Granules]

Granules may have any shape such as spherical, cylindrical, variable form or the like, and the particle size thereof is preferably a wanted particle size which is generally used (such as having a diameter of about 0.4 to about 2.0 mm).

Granules can be obtained, for example, in a manner similar to that in the methods for preparing the granule in the above manufacturing method of tablets. In addition, a commercially available spherical granule may be covered with the diarylvinylene compound or the pharmaceutically acceptable salt thereof alone, or with the diarylvinylene compound or the pharmaceutically acceptable salt thereof and each ingredient as described above, in layers, to form a granule.

In addition, according to a general method, a core (a core granule) is preparing by using each ingredient as described above excluding the inorganic substance and the colorant in a manner similar to that in the above methods, and then the resulting core granule is coated with a suspension, in which the coating composition containing the inorganic substance and/or the colorant is dispersed, to form the coated layer thereon and obtain the granules.

The coating may be carried out by using, for example, a conventionally used type such as coating machine of a pan type, coating machine of an aeration type, fluidized bed coating apparatus and coating apparatus of a tumbling flow type.

[Manufacturing Method of Fine Granules]

The fine granules may be anything so long as they are general fine granules, and, for example, fine granules, in which the amount passing through a sieve of No. 200 (75 μm) is 10% or less of the total amount, are preferable.

Fine granules can be obtained by adjusting particle sizes thereof in granulation in a manner similar to that in the above manufacturing method of granules. In addition, a core granule having desired particle size is prepared by pulverization and/or sieving the diarylvinylene compound or the pharmaceutically acceptable salt thereof, or the core granule which is obtained above, and then the resulting core granule is coated, in a manner similar to that in coating of above granules, to form the coated layer thereon and obtain the fine granules.

[Manufacturing Method of Capsules]

Capsules are obtained by filling the fine granules, granules, tablets or the like, which each are obtained, into capsule shells. The capsule shell itself may also be a capsule shell containing the inorganic substance and/or twh colorant.

The following test examples specifically illustrate effects of the present invention.

TEST EXAMPLE 1

Stability Test of Solid Formulations

According to the guideline (6 Nov. 1996) for "Photostability Testing of New Drug Substances and Products" in The International Conference on Harmonization of Technical Requirements for Registration of Pharmaceuticals for Human Use (ICH), the stability test on each of Tablets 1 to 6 (tablets containing Compound 1 (an E-isomer), and inorganic substances and/or colorants) obtained in Example 1 to 6 respectively and Tablet A (the core tablet containing Compound 1 (an E-isomer)) obtained in Comparative Examples 1 was carried out. Tablets were exposed to the light at 15,000 Lux and for 80 hours (at an overall illumination of 1,200,000 Lux·hr), respectively, using a xenon lamp as the light sources. After exposure, total amounts of an isomer of Compound 1 [(Z)-8-(3,4-dimethoxystyryl)-1,3-diethyl-7-methyl-3,7-dihydro-1H-purine-2,6-dione; a Z-isomer of Compound 1] and an dimmer of Compound 1 in each tablet were measured by sampling and analyzing by high-performance liquid chromatography (HPLC). The conditions for HPLC analysis are as follows.

Column: Inertsil ODS-2 (manufactured by GL Science); 4.6 mm I.D.×150 mm
Column temperature: 25° C.
Elution solvent: 0.05 mol/L phosphate buffer, pH 6.1/acetonitrile=3/2
Flow rate of the elution solvent: the flow rate was adjusted so that the retention time of Compound 1 will be about 12 minutes (1.2 mL/min).
Detector: ultraviolet absorptiometer (measurement wavelength: 250 nm)

The results of the stability test are shown in Table 1.

TABLE 1

|  | Tablet 1 | Tablet 2 | Tablet 3 | Tablet 4 | Tablet 5 | Tablet 6 | Tablet A |
|---|---|---|---|---|---|---|---|
| Produced amount of Z-isomer of Compound 1 (%) | nd | nd | nd | nd | nd | nd | 0.06 |
| Produced amount of dimer (%) | 0.87 | 0.09 | 0.1 | nd | nd | nd | 1.35 | nd: not detected

Table 1 shows that the formation of the Z-isomer of Compound 1 due to isomerization was completely suppressed in Tablets 1 to 6 containing titanium oxide and/or iron oxide. In addition, Table 1 shows that formation of a dimer of Compound 1 due to isomerization was significantly suppressed in the Tablets 1 to 6 containing titanium oxide and/or iron oxide. Furthermore, both of formation of the Z-isomer of Compound 1 and formation of the dimer were completely suppressed in Tablets 4 to 6 containing both titanium oxide and iron oxide. A method for stabilization containing the diarylvinylene compound or a pharmaceutically acceptable salt thereof, As results described above, by allowing an inorganic substance and/or a colorant to exist in a solid formulation containing a diarylvinylene compound or a pharmaceutically acceptable salt thereof, both isomerization and dimerization of the diarylvinylene compound or the pharmaceutically acceptable salt thereof in the solid formulation was significantly suppressed can be significantly suppressed, and thus a solid formulation containing the diarylvinylene compound or the pharmaceutically acceptable salt thereof can be given high-stability in the storage thereof. In brief, it is considered that, a solid formulation containing the diarylvinylene compound or a pharmaceutically acceptable salt thereof, which is stabilized according to the method for stabilization of the present invention, can be preserved in a stable manner as it is or as a simple package form such as a common package in transparent glass bottles or in plastic bottles, a strip package (SP package) using a laminated polyethylene-cellophane or the like, a blister package using a vinyl chloride packaging material or the like.

Excellent hardness, disintegration property and dissolution property of the solid formulation containing the diarylvinylene compound or the pharmaceutically acceptable salt thereof, which is stabilized by the present invention, can be confirmed by the following tests.

TEST EXAMPLE 2

Measurement of Hardness of Tablets

Hardness of each of the Tablet 1 obtained in Example 1 and the Tablet A obtained in Comparative Example 1 is measured by a tablet hardness tester (PTB-311, manufactured by Pharmatest).

TEST EXAMPLE 3

Disintegration Test

According to the method described in Disintegration Test of The Japanese Pharmacopoeia, Fourteenth Edition, Part I, the time required for the disintegration of each of Tablet 1 obtained in Example 1 and Tablet A obtained in Comparative Examples 1 is measured using distilled water as a test fluid.

TEST EXAMPLE 4

Dissolution Test

According to the method 2 (puddle method) described in Dissolution Test of The Japanese Pharmacopoeia, Fourteenth Edition, Part I, each of Tablet 1 obtained in Example 1 and Tablet A obtained in Comparative Examples 1 is applied to the dissolution test. The tests are carried out using 900 mL of an aqueous solution of 2.0 wt % Tween 80 (manufactured by Wako Pure Chemical Industries Ltd.) as the dissolution medium, and the puddle is rotated at the number of 50 rotations per minute. Since the dissolution test started, the amount of Compound 1 dissolved from each tablet is measured by sampling the dissolution medium with passage of time and analyzing by HPLC. The conditions for HPLC analysis were the same conditions as shown in Test Example 1.

The present invention is described in more detail in the following Examples. However, these Examples never limit the present invention.

BEST MODE FOR CARRYING OUT THE INVENTION

Example 1

Tablet 1

A coating composition, which was prepared according to a prescription described in Table 2 below, was dispersed in distilled water to prepare a coating solution having a solid content of 15 wt %. The core tablets (1000.0 g) obtained in Comparative Example 1 were coated with a coated layer, in which the coated layer is at 5 parts by weight per 100 parts by weight of the core tablet in a dry state, by Hi-Coater (Freund Corporation, HCT-30) to obtain desired tablets.

Example 2

Tablet 2

In a manner similar to that described in Table 2, the core tablets obtained in Comparative Example 1 were coated using a coating composition, which was prepared according to a prescription described in Table 2 below, to obtain desired tablets.

Example 3

Tablet 3

In a manner similar to that described in Table 2, the core tablets obtained in Comparative Example 1 were coated using a coating composition, which was prepared according to a prescription described in Table 2 below, to obtain desired tablets.

Example 4

Tablet 4

In a manner similar to that described in Table 2, the core tablets obtained in Comparative Example 1 were coated using a coating composition, which was prepared according to a prescription described in Table 2 below, to obtain desired tablets.

Example 5

Tablet 5

In a manner similar to that described in Table 2, the core tablets obtained in Comparative Example 1 were coated using a coating composition, which was prepared according to a prescription described in Table 2 below, to obtain desired tablets.

Example 6

Tablet 6

In a manner similar to that described in Table 2, the core tablets obtained in Comparative Example 1 were coated using a coating composition, which was prepared according to a prescription described in Table 2 below, to obtain desired tablets.

Comparative Example 1

Tablet A (Core Tablets)

According to the prescription described in Table 2, core tablets were prepared as follows. Namely, using a fluid-bed granulator with solution spray system (Gratt WSG-15, manufactured by Powrex), Compound 1 (1153.8 g) obtained in a manner similar to that in Japanese Published Unexamined Patent Application No. 040652/97, lactose (8850.0 g, Parmatose, 200M Lactose, manufactured by DMV), microcrystalline cellulose (3796.2 g, Avicel PH301, manufactured by Asahi Kasei) and crospovidone (750.0 g, PVPP, XL-10, manufactured by ISP) were mixed and then an aqueous solution (3750.0 g) of 8.0 wt % polyvinyl alcohol (EG-05, manufactured by Nippon Synthetic Chemical Industry Co., Ltd.) was sprayed on the resulting mixture to prepare a granule. After drying, the resulting granule was milled by a milling machine (Fiole Type F-0 manufactured by Tokujyu Industry Co., Ltd.) to prepare a milled granule. The resulting milled granule (6930.0 g) and magnesium stearate (70.0 g, HyQual® manufactured by Mallinckrodt Inc.) were mixed by a blender (V-blender Type V-10 manufactured by Tokujyu Industry Co., Ltd.) to prepare a granule for tableting. The resulting granule for tableting was tableted by a tableting machine-(Correct 12 manufactured by Kikusui Seisakusho Ltd.) to obtain Tablet 1 (tablet weight: 130 mg; tablet shape: round shape (7.0 mmΦ)).

TABLE 2

|  | Ex. 1 | Ex. 2 | Ex. 3 | Ex. 4 | Ex. 5 | Ex. 6 | Comp. Ex. 1 |
|---|---|---|---|---|---|---|---|
| (Core Tablet) | | | | | | | |
| Compound 1 | 10.0 | 10.0 | 10.0 | 10.0 | 10.0 | 10.0 | 10.0 |
| Lactose | 76.7 | 76.7 | 76.7 | 76.7 | 76.7 | 76.7 | 76.7 |
| Microcrystalline cellulose | 32.9 | 32.9 | 32.9 | 32.9 | 32.9 | 32.9 | 32.9 |
| Crospovidone | 6.5 | 6.5 | 6.5 | 6.5 | 6.5 | 6.5 | 6.5 |
| Polyvinyl alcohol | 2.6 | 2.6 | 2.6 | 2.6 | 2.6 | 2.6 | 2.6 |
| Magnesium stearate | 1.3 | 1.3 | 1.3 | 1.3 | 1.3 | 1.3 | 1.3 |
| (Coating Composition) | | | | | | | |
| HPMC 2910 | 2.78 | 3.51 | 3.51 | 2.60 | 2.60 | 2.60 | |
| Lactose | 1.43 | 1.43 | 1.43 | 1.43 | 1.43 | 1.43 | |
| Macrogol 4000 | 0.52 | 0.52 | 0.52 | 0.52 | 0.52 | 0.52 | |
| Triacetin | 0.39 | 0.39 | 0.39 | 0.39 | 0.39 | 0.39 | |
| Titanium oxide | 1.38 | | | 1.38 | 1.38 | 1.38 | |
| Talc | | 0.47 | 0.47 | | | | |
| Yellow ferric oxide | | 0.18 | | 0.18 | | 0.082 | |
| Red ferric oxide | | | 0.18 | | 0.18 | 0.098 | |
| Total Amount | 136.5 | 136.5 | 136.5 | 136.5 | 136.5 | 136.5 | 130.0 |

INDUSTRIAL APPLICABILITY

The present invention provides a method for stabilization of a diarylvinylene compound or a pharmaceutically acceptable salt thereof in a solid formulation containing the diarylvinylene compound or the pharmaceutically acceptable salt thereof (for example, a method of suppressing isomerization, dimerization or the like at the vinylene moiety of the diarylvinylene compound).

The invention claimed is:

1. A method for suppressing formation of impurities due to dimerization of a (E)-8-(3,4-dimethoxystyryl)-1,3-diethyl-7-methyl-3,7-dihydro-1H-purine-2,6-dione represented by the compound of formula (IB)

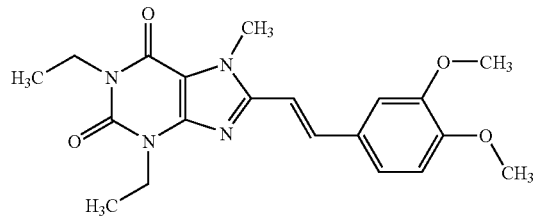

(IB)

or a pharmaceutically acceptable salt thereof, in a pharmaceutical composition wherein said pharmaceutical composition is a solid formulation containing the formula (IB) compound or the pharmaceutically acceptable salt thereof, which comprises the step of providing iron oxide in the solid formulation, wherein formation of impurities due to dimerization of the formula (IB) compound or the pharmaceutically acceptable salt thereof is suppressed.

2. The method according to claim 1, wherein the solid formulation consists of:
a core consisting of the formula (IB) compound or the pharmaceutically acceptable salt thereof and optionally one or more members selected from the group consisting of a diluent, a binder, a disintegrator, a lubricant, a surfactant, a plasticizer and an inorganic substance; and
a coated layer containing the iron oxide, wherein said core bears said coated layer.

3. The method according to claim 2, wherein the coated layer further contains at least one inorganic substance selected from the group consisting of titanium oxide, zinc oxide, magnesium oxide, talc, magnesium silicate, synthetic aluminum silicate, magnesium carbonate, calcium sulfate, aluminum sulfate and barium sulfate.

4. The method according to claim 2, wherein the coated layer contains 0.01 to 70 parts by weight iron oxide per 100 parts by weight of the coated layer.

5. The method according to claim 3, wherein the coated layer contains 0.01 to 70 part(s) by weight of the iron oxide per 100 parts by weight of the coated layer, and wherein the total amount of the inorganic substance and iron oxide is 0.01 to 90 part(s) by weight per 100 parts by weight of the coated layer.

6. The method according to any one of claims 1 and 2-5, wherein the solid formulation comprises 0.001 to 10,000 parts by weight of iron oxide per 100 parts by weight of the formula (IB) compound or the pharmaceutically acceptable salt thereof.

* * * * *